United States Patent [19]

Matsumoto et al.

[11] Patent Number: 6,010,722
[45] Date of Patent: Jan. 4, 2000

[54] ORAL REMEDY FOR RHEUMATOID ARTHRITIS AND FUNCTIONAL FOOD

[75] Inventors: Takashi Matsumoto; Yasuki Taguchi; Kotaro Fujita, all of Tsukuba; Akio Ametani, Tokyo; Syuichi Kaminogawa, Kasukabe; Masayo Nakagami, Nishinomiya, all of Japan

[73] Assignee: Nippon Meat Packers, Inc., Osaka, Japan

[21] Appl. No.: 08/981,086

[22] PCT Filed: Jun. 13, 1996

[86] PCT No.: PCT/JP96/01623

§ 371 Date: May 18, 1998

§ 102(e) Date: May 18, 1998

[87] PCT Pub. No.: WO96/41644

PCT Pub. Date: Dec. 27, 1996

[30] Foreign Application Priority Data

Jun. 13, 1995 [JP] Japan ................................. 7-171486

[51] Int. Cl.[7] .......................... A61K 47/42; A61K 38/02; A61K 38/39; A23L 1/305
[52] U.S. Cl. .......................... 424/548; 424/571; 424/572; 424/5; 514/2; 514/8; 514/21; 514/825
[58] Field of Search ..................... 424/439, 456, 424/572, 571, 548; 514/8, 21, 2, 12, 825

[56] References Cited

U.S. PATENT DOCUMENTS 5,100,874  3/1992  Odake et al. .............................. 514/18

FOREIGN PATENT DOCUMENTS 7138187  5/1995  Japan .

OTHER PUBLICATIONS

B.A. Thart, et al., *Eur. J. Immunol.*, 1588–1594, 1993.

*Primary Examiner*—F. T. Moezie
*Attorney, Agent, or Firm*—Birch, Stewart, Kolasch & Birch, LLP

[57] ABSTRACT

Oral drugs and functional foods of the present invention contain type-II collagen denatured (fragmented) under specific conditions. Rheumatoid arthritis (RA) has been considered to be an autoimmune disease against type-II collagen as an antigen. Since denatured type-II collagen of the invention induces high oral immune tolerance and inhibits immune responses against type-II collagen, it can prevent and treat RA. Particularly, RA can effectively be prevented and treated by simple oral administration of type-II collagen.

12 Claims, 4 Drawing Sheets

A: Autoclaved for 20 min at 120°C

B: Heat-treated for 20 min at 100°C

C: Heat-treated for 20 min at 65°C

D: Native type-II collagen

Fig. 5

ORAL REMEDY FOR RHEUMATOID ARTHRITIS AND FUNCTIONAL FOOD

TECHNICAL FIELD

This invention provides oral drugs and functional foods for treating and preventing rheumatoid arthritis. More particularly, the invention provides drugs and functional foods containing denatured type-II collagen to effectively treat and prevent rheumatoid arthritis.

BACKGROUNDS OF THE INVENTION

Rheumatoid arthritis (referred to as RA in the following description) is one of chronic diseases with many patients, systemically causing inflammation in connective tissues. This disease induces nonspecific inflammation mainly in synovial membranes of joints, resulting in systemic multiple arthritis and injuries of cartilage and bone.

Although details of the mechanism have not been well clarified, RA has been considered to be an autoimmune disease related to lymphocyte antigen (HLA) DR4 and activated T cells (Lancet, 341, 283,1993). Since experimental animals given type-II collagen, a main structural protein of cartilage, exhibit symptoms morphologically similar to those of RA, type-II collagen is believed to be an autoantigen of this disease (J. Exp. Med., 146, 857, 1977; Lab. Invest., 54, 26, 1986).

Anti-rheumatoid (e.g., gold-derived drugs and D-penicillamine), non-steroidal and immunosuppressive drugs are widely used to treat RA. When notable effects are not obtained after administration of these drugs, steroidal ones are administered because of their effective anti-inflammatory and immunosuppressive properties.

RA treatment with the above-mentioned drugs is not radical but nosotropic. Since the steroidal drugs may cause severe side effects, it is indispensable to pay close attention to them and to always consider reduction and suspension of medication. The most preferable RA therapy is to reduce inflammation in cartilage by the disease-specific mechanism. The drugs to be used are preferably innoxious.

From these viewpoints, RA therapy based on immune tolerance has been paid attention. Immune tolerance is a phenomenon, by which such immune response as antibody production is never brought forth, even if animals are immunized with an antigen and again with the same antigen. Substances inducing such tolerance are termed tolerogens. Regarding the RA therapy by immune tolerance, it has been reported that RA is prevented by intravenous or intraperitoneal injection with such tolerogens as type-II collagen and peptides containing its partial sequence(J. Exp. Med., 170, 1999, 1989; J. Immunol., 151, 500,1993).

Although tolerogens are intravenously or intraperitoneally injected in the above-described therapy, injection through these routes is laborious. Moreover, repeated intravenous or intraperitoneal injections with these peptides to RA patients may cause severe allergy or shock. Therefore, simpler and safer RA therapy has been desired.

Functional foods capable of treating and preventing RA have also been desired, because treatment and prevention of RA by ingesting ordinary foods other than those drugs are preferable.

From these viewpoints, RA therapy by safer and simpler administration has been desired. For this purpose, treatment and prevention of RA by immune tolerance have been examined. Oral immune tolerance or mucosal immune tolerance in wide sense of the term is a phenomenon which seldom causes immune responses against an antigen, if it is taken orally. Since any antigen taken orally is absorbed through the intestinal mucosa and then processed by functions of such various tissues as Peyer's patch and epithelial cells of the intestines and the adjacent lymphocytes, portal canal and liver, administration of such antigen rarely causes allergic reaction or shock. The oral immune tolerance has been examined as immunosuppressive therapy for allergy and rejection in organ transplantation.

Intranasal administration of the antigen also induces immune tolerance which causes no systemic immune response to the antigen, since it is absorbed through the mucosa of the digestive and airway tracts and the lungs.

As for RA prevention by oral immune tolerance, prevention of collagen-induced arthritis (CIA) in mice by oral administration (intragastric administration) of native type-II collagen from bovine cartilage was reported (Proc. Natl. Acad. Sci. USA., 83, 7443,1986). This report, however, did not describe prevention of CIA with thermally-denatured type-II collagen. Another paper reported that immunogenicity (antigenicity or allergenic property) was lowered by heat treatment and that tolerogenicity of heated collagen was similar to or lower than that of native collagen (J. Clin. Invest., 69, 673–683, 1982; J. Immunol., 140,1477–1484, 1988).

A recently published U.S. Pat. No. 5,399,435 described RA therapy by oral administration of the whole type-II collagen.

The present inventors studied the oral immune tolerance with type-II collagen and conditions for heat denaturation of type-II collagen, and found that thermally denatured type-II collagen was an effective tolerogen and inhibited RA contrary to the previous reports. Namely, the inventors succeeded in finding that the conditions for heat treatment of type-II collagen previously reported were insufficient for denaturation of collagen, and that collagen receiving severer thermal treatments induced more effective oral immune tolerance than did native collagen.

Moreover, the inventors succeeded in finding that denatured type-I I collagen (fragmented one) prepared with such agents as specifically recognizing the amino acid sequences of collagen also induced more effective oral immune tolerance than did native collagen.

The present invention was accomplished on the basis of such findings. The purposes of the invention were to provide oral drugs and functional foods to effectively prevent and treat RA.

DISCLOSURE OF THE INVENTION

To solve the above-described issues, the present invention provides oral drugs containing type-II collagen denatured thermally under acidic or alkaline conditions or chemically with agents specifically recognizing the amino acid sequences as an active component.

The present invention also provides functional foods containing type-II collagen denatured thermally under acidic or alkaline conditions or chemically with agents specifically recognizing the amino acid sequences.

Since denatured type-II collagen of this invention induces highly effective oral immune tolerance, administration of the drugs and intake of the functional foods of the invention can inhibit immune responses, treating and preventing RA.

For a convenience' sake, in the present specifications the word "oral" includes intranasal, enteral and transmucosal in addition to the original meaning of the word oral.

THE BEST MODE FOR APPLYING THE INVENTION

The oral drugs and functional foods for RA of the present invention contain type-II collagen denatured thermally or chemically with the agents specifically recognizing the amino acid sequences.

Generally, a collagen molecule consists of triple-stranded helical rods. Each rod is a polypeptide chain ($\alpha$ chain) comprising about a thousand amino acid residues (molecular weight; approximately 100,000), of which essential elements are repeats of -Gly-X-Y- (X and Y mean amino acid residues). Up to the present, 19 different types of collagen proteins (types I to XIX) have been found. Of them, type-II collagen consists of three $\alpha$-1(II) polypeptide chains, found in large amounts mostly in articular cartilage, vertebral pulp of disk and vitreous body of eye.

In the present invention, type-II collagen can be purified and isolated by conventional methods from raw materials. For example, type-II collagen is prepared by partial digestion of tissues containing type-II collagen with such proteases as pepsin and pronase, and then purification by the differential salting-out method (see J. Exp. Med., 146, 857–868,1977; Arthritis Rheum., 22, 1344,1979; J. Immunol., 124, 2912,1980 and the like). Type-II collagen commercially available is also useful. Origins of type-II collagen are not necessarily restricted. Examples of the origins are as follows; such mammalia as cattle, pigs, goats, sheep, horses, human, monkeys, rabbits, mice, and rats, such birds as chickens, turkeys, and ostriches, such reptiles as turtles and snakes, and such fishes as tunas, bonitos, salmons, sharks, and rays.

Type-II collagen synthesized chemically based on the information about the amino acid sequences of collagen of the above-described animal species or by the recombinant DNA technology can be used.

Thermally denatured type-II collagen of the invention is prepared by heating type-II collagen under acidic or alkaline conditions. As shown later in examples, such thermal-denaturation treatments result in fragmentation of the type-II collagen molecule.

Although the conditions for the thermal denaturation may vary depending on the heating temperature and period, heating for longer than 10 min at a temperature higher than 60° C. is usually adopted. Furthermore, heating for longer than 15 min at a temperature higher than 65° C. is preferable, and autoclave is even more preferable (e.g., heating for about 15 min at 121° C.).

To provide acidic conditions, organic or inorganic acid solutions are useful; e.g., citric, acetic and hydrochloric acids. The pH range is preferably below 5.5 and more preferably between 2.0 and 4.5. To provide alkaline conditions, organic or inorganic alkali solutions are useful; e.g., sodium hydroxide, potassium hydroxide, and triethanolamine. The pH range is preferably above 9.5 and more preferably between 10.0 and 12.0.

The thermal denaturation conditions can be at a pH between 2.0 and 4.5 or between 10.0 and 12.0, at a temperature between 100 and 120° C., for a period between 10 and 15 minutes.

The thermal-denaturation conditions are heating type-II collagen in an inorganic or organic acid solution for longer than 15 min or preferably for longer than 20 min at above 65° C. or more preferably at about 100° C.; or heating in an autoclave for longer than 30 min or preferably for 2 to 10 h at about 110° C., or for longer than 15 min or preferably for 20 min at about 120° C.

As shown in the examples, thermally denatured type-II collagen thus obtained contains partially disintegrated cleaved substances with a molecular weight lower than that of the $\alpha$-1 polypeptide chain of type-II collagen.

Another invention related to denatured type-II collagen is type-II collagen denatured (fragmented) with the agents specifically recognizing the amino acid sequences.

To denature (fragment) type-II collagen with the agents specifically recognizing the amino acid sequences, a large number of site-specific agents and their recognition sites are known and commercially available. Examples are as follows (the cleavage sites are indicated with ↓): Hydroxylamine: Asn ↓ Gly, formic acid: Asp ↓ Pro, acetic acid: Asp ↓ Pro, BMPS-skatole: Trp ↓ and o-iodosobenzoic acid: Trp ↓ are the examples of chemical agents. Chymotrypsin: Trp ↓ and Phe ↓, collagenase: Pro-X ↓ Gly-Pro, endoproteinase Lys-C: Lys ↓, thrombin: Arg-Gly-Pro-Arg ↓, and trypsin: Arg ↓ and Lys ↓ are the examples of proteolytic enzymes.

These agents may be used solely or in combination of more than two agents. Although kinds, amounts, and reaction temperatures of the agents may conventionally be decided, they are favorably used after unfolding the triple-stranded helical structure of type-II collagen by heating for longer than 10 min at higher than 30° C.

To remove or inactivate the agents used for denaturation (fragmentation), such methods that are commonly known by those skilled in the art are used; e.g., heating, dialysis, ultrafiltration, ion exchange chromatography, and pH adjustment.

Type-II collagen or that denatured thermally or with the agents specifically recognizing the amino acid sequences (for convenience' sake, these are both referred to as denatured type-II collagen in the following description) may be used as the drugs or the functional foods of the invention with or without purification by conventional methods (e.g., salting out, dialysis, gel filtration, ultrafiltration, and ion exchange chromatography) or powdering after lyophilization.

The above-described denatured type-II collagen characteristically possesses a lower immunogenicity and a higher tolerogenicity than does native type-II collagen. Moreover, since denatured type-II collagen is derived from a living-body composition, it is presumed to be highly safe. With these viewpoints, the examples described later show that the increase in the arthritis rate, arthritic index and arthritic-paw rate of the CIA mice given intranasally denatured type-II collagen and then immunized with native collagen was inhibited and delayed.

Inhalation of thermally denatured type-II collagen by mice at such a high dose as 200 μg inhibited production of the antigen-specific antibodies (IgG1, IgG2a and IgG2b) and an inflammatory cytokine, IFN-γ. Such a phenomenon is known as anergy or clonal paralysis.

The inhalation of thermally denatured collagen by mice at such a low dose as 0.2, 2 or 20 μg did not inhibit production of IgG1 itself, but inhibited that of inflammation-related IgG2a and IgG2b and enhanced that of anti-inflammatory cytokine IL10. Such a phenomenon is known as active or by-stander suppression.

Furthermore, the present inventors consider that the denaturation treatments by heat or with the agents reduce the molecular weight of type-II collagen and destroy its steric molecular structure, and that denatured type-II collagen having the destructed helical structure is safer causing less side effects than does native type-II collagen, since the antibodies produced by B lymphocytes can specifically recognize the helical steric structure of type-II collagen molecule to bind it.

The methods to denature type-II collagen are not restricted to the above-described examples but may be changed according to the circumstances. For examples, thermally denatured type-II collagen may be formulated in final products (e.g., such foods as meat products and fish products, such dairy products as milk, such beverages as juice and tea, and such drugs as liquid drugs and transintestinal liquid) by incorporation of native type-II collagen in their recipes as a raw material and then pasteurization. Products containing thermally denatured type-II collagen (e.g., soup) may also be prepared by hot-water extraction of raw materials containing type-II collagen (e.g., cartilage of joints of domestic animals).

The drugs for RA treatment of the invention contain the above-described denatured type-II collagen as an active component and may orally be administered to treat and prevent RA (the word "orally" comprehensively includes meanings of intranasally, transintestinally and transmucosally).

The active component of denatured type-II collagen can be blended with solid or liquid innoxious pharmaceutical carriers prepared in various pharmaceutical forms and administered. Examples of pharmaceutical forms are oral drugs (e.g., such solid drugs as tablet, granule, powder, and capsule, such liquid ones as solution, suspension, and emulsion, and lyophilized one), inhalants, suppositories, and transintestinal liquid. These drugs may be prepared by conventional pharmaceutical practices. Examples of the above-described innoxious pharmaceutical carriers are glucose, lactose, sucrose, starch, mannitol, dextrin, fatty-acid glyceride, polyethylene glycol, hydroxyethyl starch, ethylene glycol, polyoxyethylene sorbitan fatty-acid ester, amino acids, albumin, water, and physiological saline. Furthermore, such conventional additives as stabilizer, smoother, humectant, emulsifier, and caking agent may be added.

The dosage of the drug of the invention for RA treatment may properly be adjusted depending on the age, body weight, symptoms, and severity of the disease of patients, the medication schedule, and the drug forms. For example, the dosage may range between 0.05 $\mu$g and 5 g/kg of body weight/day. It may be taken in several doses a day.

The functional foods for RA treatment of the invention contain above-described denatured type-II collagen and may be eaten as foods (or as a food additive) with or without enrichment with various nutrients or dispersion in beverages to treat and prevent RA. After adding the above-described carriers according to the conventional practices, the functional foods may be formed in shapes suitable for eating (e.g., granule, grain, tablet, capsule, and paste), added to various solid foods (e.g., such meat products as hams and sausages, such fish products as "kamaboko" [cooked fish paste] and "chikuwa" [baked fish paste], bread, and butter) and various liquid foods (potable water, juice, milk, and soft drinks).

The dosage of denatured type-II collagen formulated in various functional foods may properly be adjusted depending on the age, body weight, severity, degrees of the disease of the patient, and shape of the food. The dosage may range between 0.05 $\mu$g and 5 g/kg of body weight/day. Intake of more than those dosages, however, may be harmless, since denatured type-II collagen has no harmful effect on living bodies, even if a large amount is taken.

Industrial Applicability

As described above, RA has been considered to be an autoimmune disease against type-II collagen as the antigen. Since denatured type-II collagen of the present invention exerts a high tolerogenicity, administration of the drug or intake of the functional food of the invention can inhibit the immune responses, resulting in treating and preventing RA. The present invention can be applied to not only prevention of RA but also treatment of RA patients. Moreover, treatment and prevention of RA can be accomplished more simply and more safely by oral administration (intranasal, transintestinal and transmucosal administrations are comprehensively included) and ingestion.

EXAMPLES

The present invention will be specifically explained in detail with actual experiments and examples, but the scope of the invention is not restricted to them.

Experiment 1

Preparation of thermally denatured collagen

Thermally denatured collagen was prepared by heating bovine type-II collagen in a citric-acid solution (pH 3.0) for 15 min at 65° C. or by autoclaving collagen (for 15 min at 121° C.).

For a convenience' sake, type-II collagen denatured by heating for 15 min at 65° C. is referred to as "denatured collagen A" and that by autoclaving as "denatured collagen B" in the following description.

Experiment 2

Preparation of denatured (fragmented) collagen with the agent specifically recognizing the amino acid sequences Bovine type-II collagen was suspended in 0.1 M ammonium carbonate (concentration; 1 mg/ml), heated for 30 min at 50° C., and then digested with trypsin (TPCK-Tripsin, Sigma Chemical Co., St. Louis, Mo.: concentration, 2% of type-II collagen) for 1 h at 37° C. Enzymatic reaction was stopped by adjusting pH to 3.0 with 12 N HCl and allowing to stand overnight at 4° C. After removing undigested type-II collagen and trypsin by ultrafiltration (Centriprep 3, Amicon, Beverly, Mass.), collagen denatured (digested) with the enzyme was obtained. Type-II collagen denatured with trypsin is referred to as "denatured collagen C" in the following description for a convenience' sake.

Experiment 3

Inhibition of collagen-induced arthritis (CIA) in mice (1)

① Methods

DBA/1 mice were intranasally given denatured bovine collagen A, B or C dissolved in 10 mM citric acid (collagen content of each: 200 $\mu$g) under anesthesia 7 days before immunization. To induce CIA, the mice were immunized with a mixture of native type-II collagen and Freund's complete adjuvant (Difco Laboratories, Detroit, Mich.) on day 0 and then with that of native type-II collagen and Freund's incomplete adjuvant (Difco Laboratories)on day 21. In place of denatured collagen, the mice of test variables for comparison and control were allowed to inhale native type-II collagen and a 10 mM citric acid solution, respectively.

② Results

The period in days needed to induce CIA for each group were compared and analyzed by the Mann-Whitney U test. As shown in Table 1, native type-II collagen did not induce any immune tolerance, whereas denatured collagens A, B and C delayed onset of CIA and induced immune tolerance. The tolerogenicity of collagen A was not higher than that of denatured collagen B prepared by autoclaving and denatured collagen C prepared by the treatment with trypsin specifically cleaving the C termini of arginine and lysine residues of the amino acid sequence after unfolding the steric structure of the triple-stranded helix of α-1(II)-polypeptide chains.

TABLE 1

| Test substance | Days needed to induce CIA (mean ± SD) |
| --- | --- |
| Denatured collagen A | 41.9 ± 5.11[a] |
| Denatured collagen B | 48.3 ± 11.1[b] |
| Denatured collagen C | 48.3 ± 9.1[b] |
| Citric acid | 34.1 ± 6.70 |
| Native type-II collagen | 33.2 ± 5.80 | a: $p < 0.02$, b: $p < 0.05$

Experiment 4
Inhibition of CIA development in mice (2)
① Methods

DBA/1 mice were fed on a mixture consisting of lyophilized and then powdered chicken denatured collagen A or B (4%) and commercially available feed during a period from 31 days to a day before immunization. CIA was induced as described in Experiment 3. In place of denatured collagen, mice for comparison and control were fed on the feed mixed with native type-II collagen and casein, respectively.

② Results

Figure 1:
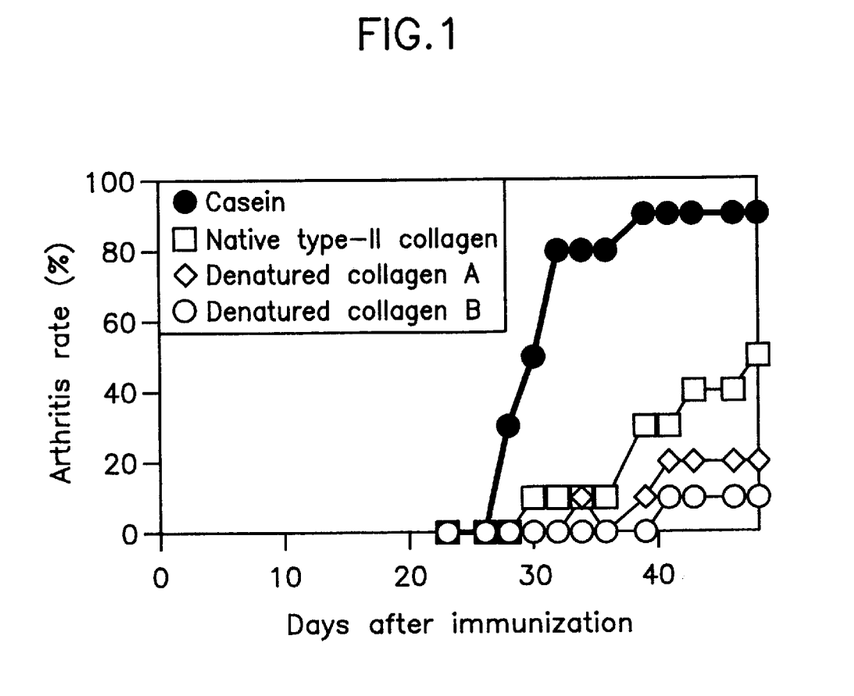
FIG. 1 shows arthritis rates of CIA mice in Example 4.

CIA arthritis rates of the mice of each group were periodically observed and analyzed by the Mann-Whitney U test. The results are shown in FIG. 1. A mouse possessing more than one paw of arthritis of a score higher than 1 was regarded as an arthritis mouse. The CIA arthritis rate (%) was calculated by dividing the sum of the arthritis mice by the total number of the mice of each group.

As shown in FIG. 1, native type-II collagen and denatured collagen A and B 30 inhibited significantly onset of CIA (p<0.01) and induced immune tolerance. The tolerogenicity of collagen A was higher than that of native type-II collagen, and that of collagen B prepared by autoclaving was much higher than that of denatured collagen A.

Experiment 5
Inhibition of CIA development by intranasal administration of denatured type-II collagen (effects of the dosage)
① Methods DBA/1 mice were intranasally given 0.2, 2, 20 or 200 μg of the bovine denatured collagen B (dissolved in 10 mM citric acid) under anesthesia 7 days before immunization. To induce CIA, the mice were immunized with a mixture of native type-II collagen (200 μg) and Freund's complete adjuvant on day 0 and then with that of native type-II collagen (200 μg) and Freund's incomplete adjuvant on day 21. After that, CIA development was observed. In place of denatured collagen B, control mice were allowed to inhale a 10 mM citric acid solution.

② Results

Figure 2:
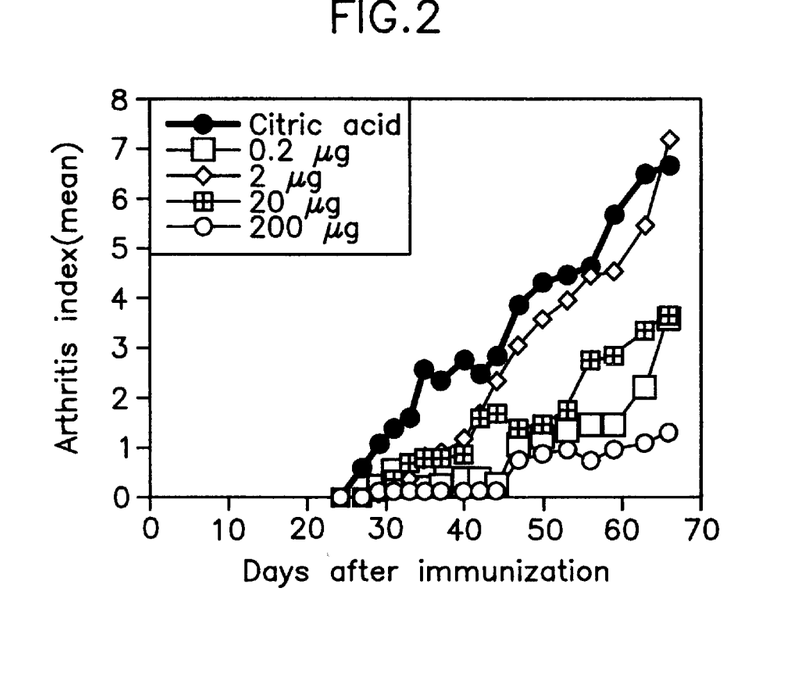
FIG. 2 shows arthritic indexes of CIA mice in Example 5.
Figure 3:
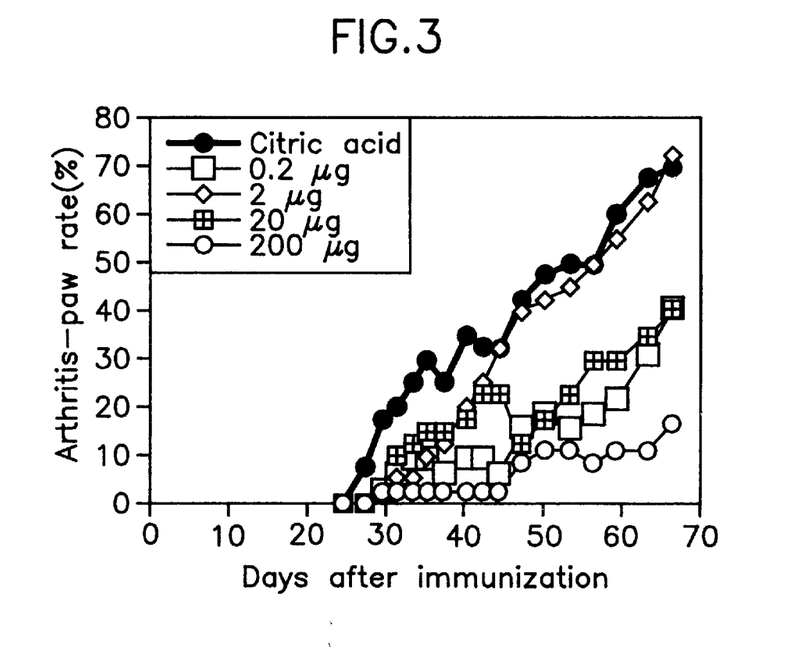
FIG. 3 shows arthritic-paw rates of CIA mice in Example 5.

The results are shown in FIGS. 2 and 3. FIG. 2 shows changes in the arthritic index of the CIA mice. The arthritic index is the mean of the sums of the arthritic scores of four paws of each mouse; the arthritic scores of 0 to 3 were given according to the degree of arthritis (swelling of the paw). FIG. 3 shows arthritic-paw rates (%) of the CIA mice. The arthritic-paw rate (%) was calculated by dividing the sum of the arthritis paws by the total number of the mouse paws of each test variable.

As shown in FIGS. 2 and 3, the arthritic indexes and the arthritic-paw rates of the control mice (namely, the mice immunized with the native type-II collagen on days 0 and 21 without previous inhalation of denatured collagen B) increased with days from immediately after the booster immunization.

On the contrary, inhalation of 200 μg of denatured collagen B remarkably inhibited and delayed the increases in the arthritic index and the arthritic-paw rate. Such tendencies were observed in the dose-dependent manner in the mice inhaling 20 or 2 μg of denatured collagen B.

Moreover, inhalation of 0.2 μg of denatured collagen B remarkably inhibited and delayed the increase in the arthritic index and the arthritic-paw rate to a similar extent as did that of 200 μg.

Example 6
Effects of intranasal administration of denatured type-II collagen on production of antibodies (subclasses) against type-II collagen Effects of intranasal administration of denatured type-II collagen on the antibody (subclass) production were examined. The IgG subclasses of IgG2a and IgG2b have been considered to be related to arthritis, since complement can bind them and induce inflammation.

Moreover, production of IgG2a has been considered to be closely related to that of IFN-γ production by T cells (Th 1 type) found in a large amount in arthritic synovial membrane of joints. In other words, decrease in antigen-specific IgG2a in serum is related to systemic decrease in the Th-1 response to the antigen.

① Methods
Collection of sample sera

In parallel with the above-described Experiment 5, blood was collected from the test variable and control mice 28 days after the immunization (namely, 7 days after the booster immunization). The sera obtained after centrifugation were subjected to titration of the anti-type 11 antibody (subclasses) by the method described below.

IgG-subclass determination by ELISA

Figure 4:
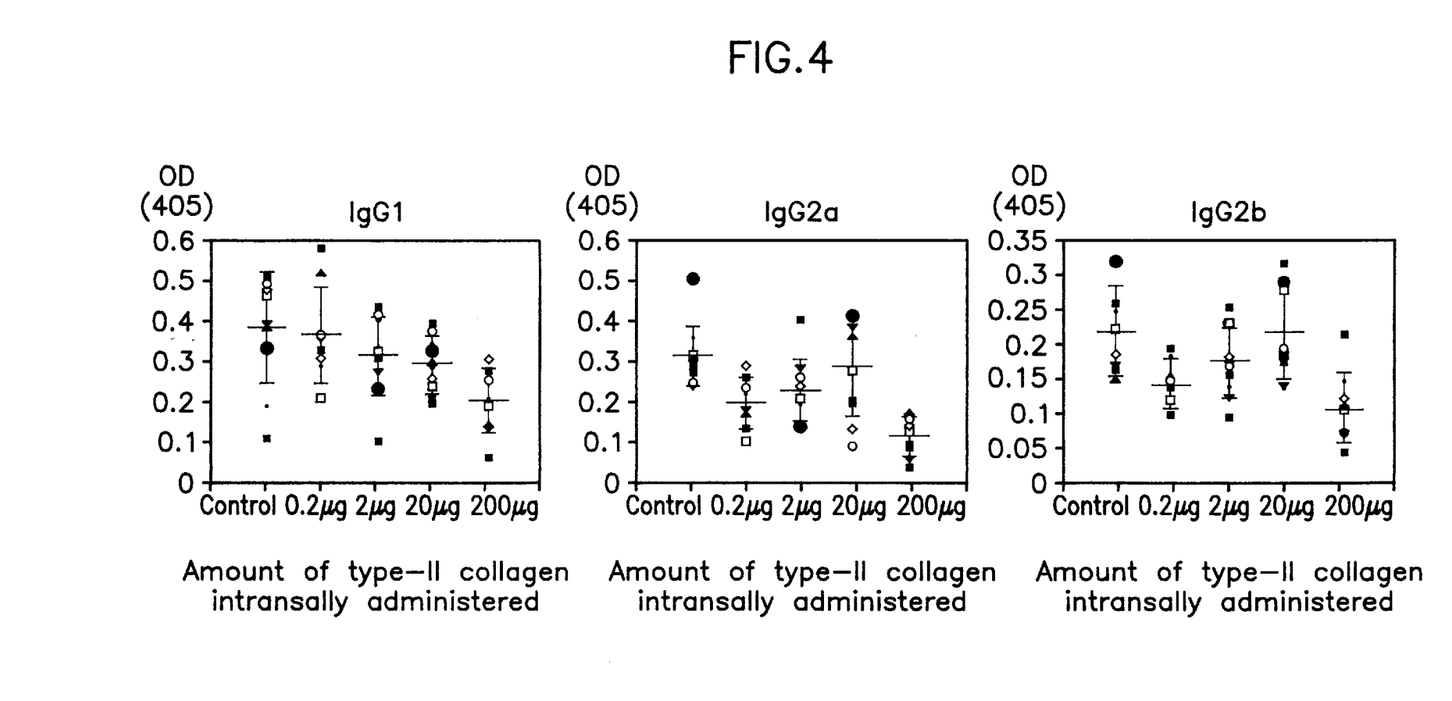
FIG. 4 shows levels of each of antibody subclass against type-II collagen in Example 6.

Native type-II collagen (5 μg/well) was adsorbed to a microplate (Maxisorp, Nunc). After washing with PBS-Tween, an appropriately diluted mouse serum was added. After washing with PBS-Tween, each of alkaline-phosphatase-conjugated rat antibodies against the mouse IgG subclasses (anti-mouse IgG1, anti-mouse IgG2a and anti-mouse IgG2b; Zymed) was added. After washing with PBS-Tween, a substrate solution (p-nitrophenyl-2-phosphate, Tokyo Kasei, Tokyo) was added and allowed to stand for 30 min. The reaction was stopped by adding 5 N NaOH, and then absorbance at 405 nm was read (FIG. 4).

② Results

The control mice (namely, the mice immunized with native type-II collagen on days 0 and 21 without previous inhalation of denatured collagen B) produced IgG1, IgG2a and IgG2b. Such results coincided with the increased arthritic indexes and arthritic-paw rates shown in FIGS. 2 and 3.

On the Contrary, inhalation of 200 μg of denatured collagen B by the mice inhibited production of IgG1, IgG2a and IgG2b. Such results were comparable to suppressed increase in the arthritic index and the arthritic-paw rate shown in FIGS. 2 and 3.

Inhalation of 20, 2 or 0.2 μg of denatured collagen B by the mice inhibited production of IgG2a and IgG2b but not that of IgG1. Particularly, the levels of IgG2a and IgG2b of the mice having inhaled 0.2 μg of denatured collagen B were equivalent to those of the mice having inhaled 200 μg. Such results were comparable to the delayed increase in the arthritic index and arthritic-paw rate shown in FIGS. 2 and 3.

From these results, intranasal administration of 20, 2 or 0.2 μg of denatured collagen B (especially, 0.2 μg) effectively inhibited production of IgG2a and IgG2b, both of which are believed to be related to the symptoms of arthritis due to their complement-binding ability. Moreover, since production of IgG1 itself was not inhibited by the administration of 20, 2 or 0.2 μg of denatured collagen B, production of the antibodies capable of recognizing and excluding foreign substances may have not been inhibited.

Experiment 7

Cytokine production by lymphocytes isolated from the mice intaranasally given denatured type-II collagen (effects of stimulation by denatured type-II collagen)

Cytokines (IFN-γ and IL-10) related to inflammation were determined to examine the effects of stimulation with denatured type-II collagen on production of these cytokines.

TGF-β and IL-10 are known as anti-inflammatory (suppressive) cytokines and immunologically important modulators of RA (J. Exp. Med., 179, 15617–15627, 1994).

① Methods

Isolation and culture of lymphocytes

Similarly to Experiment 5, DBA/1 mice were intranasally given under anesthesia 0, 0.002, 0.02, 0.2, 2, 20 or 200 μg of bovine denatured collagen B. These mice were subcutaneously immunized in their hind paws with a mixture of native type-II collagen (100 μg) and Freund's complete adjuvant (Difco) on day 0.

Ten days later, popliteal lymph nodes were aseptically excised from each mouse. Then, cell suspensions of a single population were prepared and placed ($1 \times 10^6$ cells/well) in a 96-well microplate (Falcon). After adding serum-free culture medium (X-vivo 20, Biowhittaker) and type-II collagen (final concentration; 500 μg/ml) to each well, the plates were incubated for 3 days under 5% $CO_2$. After that, the supernatant fluid of the culture medium was collected.

Similarly, the cells were cultured without collagen or with concanavalin A (final concentration; 5 μg/ml ) in place of collagen. The culture fluid was collected. Since concanavalin A is a mitogen of T cells, it was used to stimulate nonspecifically all the T cells as a positive control.

Determination of cytokines by sandwich ELISA

Rat monoclonal antibodies against mouse cytokines (anti-mouse IL-10 monoclonal antibody, JES5-2A5; anti-mouse IFN-γ monoclonal antibody, RA-6A2; Pharmingen) were coated (50 μl/well) on a microplate (Maxisorp, Nunc). After washing with PBS-Tween, the plate was blocked with 3% BSA-added PBS-Tween. Then, the appropriately diluted culture supernatant described above were added to each well.

After washing with PBS-Tween, each of biotin-conjugated rat monoclonal antibodies against mouse cytokines (anti-mouse IL-10 monoclonal antibody, SXC-1; anti-mouse IFN-γ monoclonal antibody, XMG1.2; Pharmingen) was added to the wells.

After washing with PBS-Tween, avidin-labeled alkaline phosphatase (Zymed) was added. After washing with PBS-Tween, a substrate solution (p-nitrophenyl-2-phosphate, Tokyo Kasei, Tokyo) was added to each well and the mixture was allowed to stand for 60 min. The reaction was stopped by adding 5 N NaOH. The concentrations of INF-γ and IL-10 produced were determined from the absorbance at 405 nm and compared with those of the control samples (the amount of denatured collagen B administered; 0). The results are shown in Table 2.

TABLE 2

| Amount of denatured collagen B intranasally administered (μg) | IFN-γ | IL-10 |
| --- | --- | --- |
| 200 | ↓↓ | ↓ |
| 20 | ↓ | ↓ |
| 2 | → | ↑ |
| 0.2 | → | ↑↑ |
| 0.02 | → | ↑↑ |
| 0.002 | → | ↑↑ |

↑↑: Production of cytokine was obviously stimulated in comparison with the control.
↑: Production of the cytokine tended to be stimulated in comparison with the control.
→: Production of cytokine was not different from the control.
↓: Production of cytokine tended to be inhibited in comparison with the control.
↓↓: Production of cytokine was obviously inhibited in comparison with the control.

② Results

Mouse lymphocytes proliferated evenly in the concanavalin-A-added medium (positive control), whereas only collagen-reactive lymphocytes proliferated and produced colonies in the type-II collagen-added media. Cytokines produced by these collagen-reactive lymphocytes were determined. The results were as follows;

Inflammatory IFN-γ was inhibited more clearly by the lymphocytes isolated from the mice having inhaled 200 μg of denatured collagen B and then cocultured with type-II collagen than those from the mice without inhalation and then cocultured likewise (control).

Production of anti-inflammatory IL-10 was stimulated more clearly by the lymphocytes isolated from the mice intranasally given 0.002, 0.02, 0.2 or 2 μg of denatured collagen B and then cocultured with type-II collagen than those from the mice without inhalation and then cocultured likewise (control). More particularly, IL-10 production was stimulated by lymphocytes from the mice having inhaled 0.2 or 0.02 μg of denatured collagen B and then cocultured with type-II collagen.

Experiment 8

Examination of thermally denatured collagen

Figure 5:
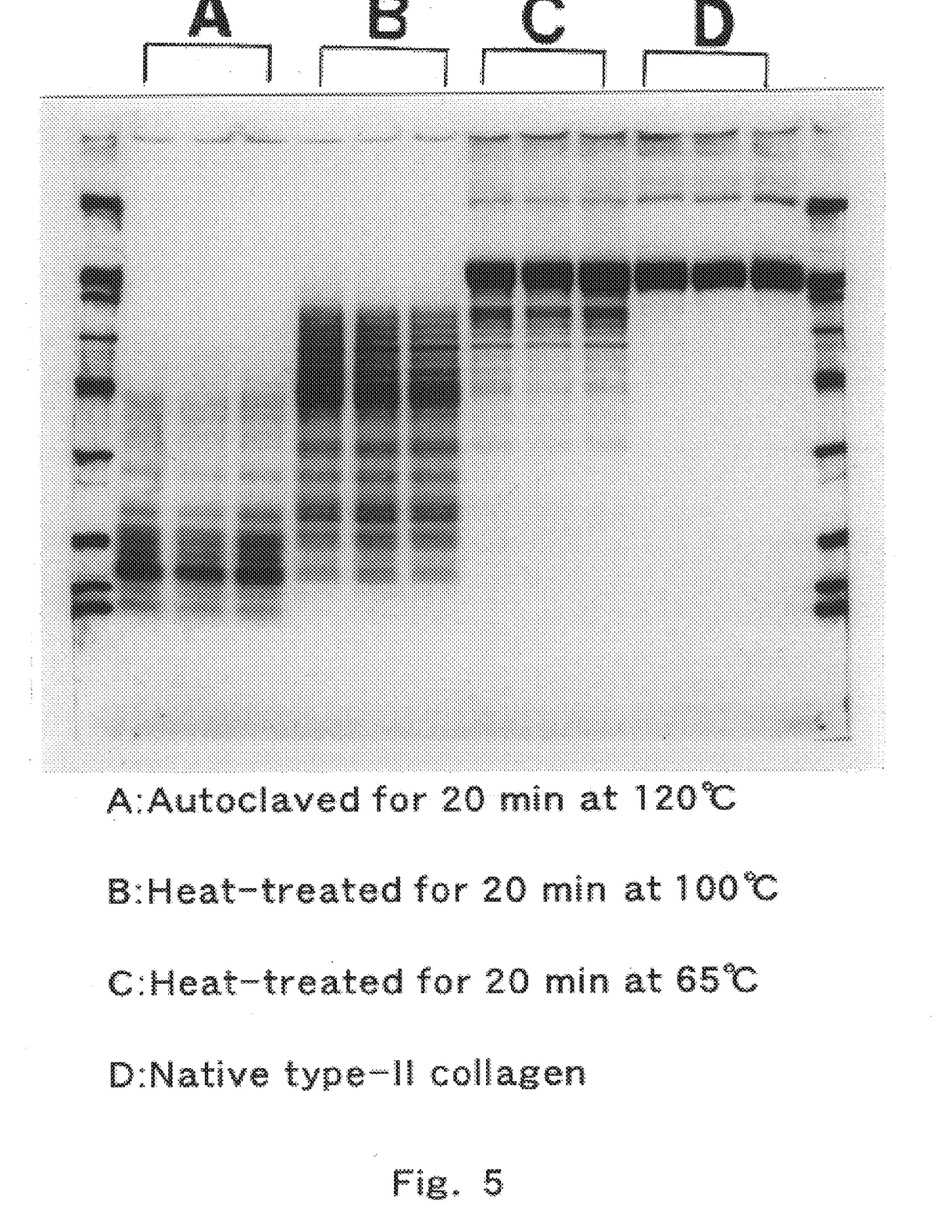
FIG. 5 is an electrophoresis profile of thermally denatured type-II collagen in Example 8.

To characterize thermally denatured collagen, chicken type-II collagen was dissolved at 0.1, 0.3 and 1% in 10 mM citric acid (pH 3.0). The solutions were heated for 20 min at 65° C., for 20 min at 100° C. or autoclaved for 20 min at 120° C. Denatured collagen was electrophoresed. The results are shown in FIG. 5, where A, B, C, and D denote collagen autoclaved (for 20 min at 120° C.), that heated for 20 min at 100° C., that heated for 20 min at 65° C. and that untreated, respectively. The concentrations of every three lanes are 0.1, 0.3 and 1.0% from left to right. Both ends are molecular markers.

As illustrated in FIG. 5, native chicken type-II collagen consisted of α-1 chain (MW: 100,000). Thermal denaturation increased the amounts of lower molecular-weight substances. The α-1 chain disappeared in the samples heated for 20 min at 100° C. and those autoclaved for 20 min at 120° C. Therefore, the partially destructed substances seemed to act as tolerogens.

With bovine type-II collagen, similar experiments as described above were carried out and almost the same electrophoresis profiles as FIG. 5 were obtained.

The electrophoresis profile of denatured bovine collagen C also showed disappearance of the α-1 chain. Denatured collagen C contained much lower molecular-weight substances than the autoclaved (for 20 min at 120° C.) specimen. Decomposed substances with molecular weights lower than 10,000 were observed. Therefore, partially decomposed substances of lower molecular weights seemed to act as tolerogens.

Experiment 9

Thermally denatured type-II collagen was prepared by the thermal treatment as described in Experiment 1 except for using a sodium hydroxide solution (pH 11.0) in place of the citric acid solution.

Example 1

| Denatured bovine dcollagen A | 0.5 mg |
| Magnesium stearate | 5 mg |
| Corn starch | 20 mg |
| Lactose | 174.5 mg |

The mixture was conventionally formed into tablets.

Example 2

| Denatured chicken collagen B | 0.5 mg |
| Magnesium stearate | 5 mg |
| Lactose | 194.5 mg |

The mixture was conventionally put into gelatin hard capsules.

Example 3

| Denatured bovine collagen C | 0.5 mg |
| Magnesium stearate | 5 mg |
| Lactose | 194.5 mg |

The mixture was conventionally put into gelatin hard capsules.

Example 4

Denatured bovine collagen B and natural juice (concentrated juice was rehydrated before use) were blended at a ratio of 0.5 mg to 200 ml, sterilized conventionally and packaged aseptically to obtain a juice product.

Example 5

Ground meat for Wiener sausage was blended with bovine type-II collagen B at a ratio of 15 g to 30 μg, stuffed into sheep casing, smoked, pasteurized, chilled and packaged. Wiener sausage was thus prepared.

Example 6

Wiener sausage was prepared as described in Example 5 except for using bovine denatured collagen C in place of bovine denatured collagen B.

Example 7

To 150 g of chicken sternal cartilage (so-called ensiform cartilage) 1000 ml of water was added, to which such aromatic vegetables as onion, carrot, parsley, celery, and ginger, and pepper were added. It was simmered for 3 h, chilled, filtered through a strainer, seasoned again with salt and pepper.

The chicken soup thus prepared was electrophoresed. The same electrophoresis profile as shown in FIG. 5 was obtained. Western-blotting analysis with rat anti-chicken type-II collagen antibody showed that the soup contained denatured type-II collagen.

We claim:

1. A functional food containing a type-II collagen denatured thermally under acidic or alkaline conditions or enzymatically with a site-specific proteolytic enzyme.

2. A functional food claimed in claim 1, wherein the type-II collagen denatured thermally is prepared by healing type-II collagen for 10 min or more at 60° C. or higher, and that the type-II collagen denatured enzymatically is prepared by heating the type-II collagen for 10 min or more at 30° C. or higher, to unfold the steric structure of the triple-stranded helix of α 1(II)-polypeptide chains, and then processing unfolded type-II collagen with a site-specific proteolytic enzyme.

3. The functional food claimed in claim 2, wherein said proteolytic enzyme is chymotrypsin, collagenase, endoproteinase, thrombin or trypsin.

4. The functional food claimed in claim 3, wherein said proteolytic enzyme is trypsin.

5. The functional food claimed in claim 1, in which conditions for thermal denaturation comprise heating at a pH between 2.0 and 4.5 or between 10.0 and 12.0, at a temperature between 100 and 120° C., for a period between 10 and 15 min.

6. The functional food claimed in claim 1, in which type-It collagen originates from a mammal, bird, reptile or fish.

7. The functional food claimed in claim 6, wherein said mammal is a cow, pig, coat, sheep, horse, human, monkey, rabbit, mouse or rat, said bird is a chicken, turkey or ostrich, said reptile is a turtle or snake, and said fish is a tuna, bonito, salmon, shark or ray.

8. The functional food claimed in claim 1, wherein said proteolytic enzyme is chymotrypsin, collagenase, endoproteinase, thrombin or trypsin.

9. The functional food claimed in claim 8, wherein said proteolytic enzyme is trypsin.

10. The method of treating rheumatoid arthritis comprising administering a therapeutically effective amount of a type-II collagen which has been thermally denatured under acidic or alkaline condition or enzymatically denatured with a site-specific proteolytic enzyme.

11. The method claimed in claim 10, wherein said proteolytic enzyme is chymotrypsin, collagenase, endoproteinase, thrombin or trypsin.

12. The method claimed in claim 11, wherein proteolytic enzyme is trypsin.

* * * * *